(12) United States Patent
Senaratne

(10) Patent No.: US 10,233,478 B2
(45) Date of Patent: Mar. 19, 2019

(54) PROCESS FOR REDUCING CO2 EMISSIONS AND INCREASING ALCOHOL PRODUCTIVITY IN SYNGAS FERMENTATION

(71) Applicant: INEOS BIO SA, Lisle, IL (US)

(72) Inventor: Ryan Senaratne, Fayetteville, AR (US)

( * ) Notice: Subject to any disclaimer, the term of this patent is extended or adjusted under 35 U.S.C. 154(b) by 41 days.

(21) Appl. No.: 14/017,903

(22) Filed: Sep. 4, 2013

(65) Prior Publication Data

US 2014/0080195 A1     Mar. 20, 2014

Related U.S. Application Data

(60) Provisional application No. 61/702,824, filed on Sep. 19, 2012, provisional application No. 61/702,826, (Continued)

(51) Int. Cl.
| | | |
|---|---|---|
| *C12Q 1/04* | (2006.01) | |
| *C12P 7/06* | (2006.01) | |

(Continued)

(52) U.S. Cl.
CPC ............... *C12Q 1/04* (2013.01); *C12P 7/065* (2013.01); *C12P 7/08* (2013.01); *C12Q 3/00* (2013.01);
(Continued)

(58) Field of Classification Search
CPC ... C12Q 1/04; C12Q 3/00; C12P 7/065; C12P 7/08; G01N 21/31; G01N 33/84; Y02E 50/17
(Continued)

(56) References Cited

U.S. PATENT DOCUMENTS

| | | | |
|---|---|---|---|
| 5,173,429 A | 12/1992 | Gaddy | |
| 5,593,886 A * | 1/1997 | Gaddy | ...................... C12P 7/56 435/140 |
| 5,807,722 A | 9/1998 | Gaddy | |
| 6,136,577 A | 10/2000 | Gaddy | |
| 6,774,148 B2 | 8/2004 | O'Rear | |
| 7,285,402 B2 | 10/2007 | Gaddy | |
| 2011/0104770 A1* | 5/2011 | Tobey | .......................... 435/140 |

FOREIGN PATENT DOCUMENTS

| | | |
|---|---|---|
| WO | WO 2011/139163 | 11/2011 |
| WO | WO 2012/015317 | 2/2012 |

OTHER PUBLICATIONS

Kundiyana et al., Effect of nutrient limitation and two-stage continuous fermentor design on productivities during "Clostridium ragsdalei" syngas fermentation, Bioresource Technology, 102 (2011), pp. 6058-6064.*

(Continued)

*Primary Examiner* — Jennifer M. H. Tichy
(74) *Attorney, Agent, or Firm* — James P. Krueger

(57) ABSTRACT

A process is provided that is effective for reducing $CO_2$ emissions, enhancing STY and/or increasing cell density. The process allows for utilization of syngas from different sources by controlling concentration levels of CO, $CO_2$ and $H_2$ in syngas provided to the fermentation and by controlling relative concentrations of CO, $CO_2$ and $H_2$ in the syngas provided to the fermentation. The process includes providing syngas to a first fermentation zone and fermenting the syngas. If the first fermentation zone off-gas includes about 4 mole % or more CO, then at least a portion of the first fermentor off-gas is provided to one or more subsequent fermentation zones.

8 Claims, 3 Drawing Sheets

Related U.S. Application Data filed on Sep. 19, 2012, provisional application No. 61/702,832, filed on Sep. 19, 2012, provisional application No. 61/702,837, filed on Sep. 19, 2012.

(51) Int. Cl.
*C12P 7/08* (2006.01)
*C12Q 3/00* (2006.01)
*G01N 21/31* (2006.01)
*G01N 33/84* (2006.01)

(52) U.S. Cl.
CPC ............. *G01N 21/31* (2013.01); *G01N 33/84* (2013.01); *Y02E 50/17* (2013.01)

(58) Field of Classification Search
USPC .......................................................... 435/163
See application file for complete search history.

(56) References Cited

OTHER PUBLICATIONS

Hurst, Kendall et al., "Carbon monoxide partial pressure effects on the metabolic process of syngas fermentation" Biochemical Engineering Journal, Sep. 22, 2009, 48(2010) 159-165.

Kundu, Suman et al. "Direct Measurement of Equilibrium Constants for High-Affinity Hemoglobins" Biophysical Journal, Jun. 2003, vol. 84 3931-3940.

Riggs, Seth et al. "Measuring Carbon Monoxide Gas-Liquid Mass Transfer in a Stirred Tank Reactor for Syngas Fermentation" Biotechnol, 2006, 22, 903-906.

\* cited by examiner

PROCESS FOR REDUCING CO2 EMISSIONS AND INCREASING ALCOHOL PRODUCTIVITY IN SYNGAS FERMENTATION

This application claims the benefit of U.S. Provisional Application Nos. 61/702,824, 61/702,826, 61/702,832 and 61/702,837, all filed on Sep. 19, 2012, all of which are incorporated in their entirety herein by reference.

A process is provided that is effective for reducing $CO_2$ emissions and increasing alcohol productivity from a syngas fermentation. More specifically, relative amounts of CO, $CO_2$ and $H_2$ in the syngas are controlled to minimize $CO_2$ emissions and/or enhance total alcohol STY in the syngas fermentation. The process may include utilization of one or more fermentation zones.

BACKGROUND

Anaerobic microorganisms can produce alcohols and other products from carbon monoxide (CO) through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a method and apparatus for converting waste gases into organic acids and alcohols using *Clostridium ljungdahlii* ATCC No. 55380. U.S. Pat. No. 6,136,577 describes a method and apparatus for converting waste gases into ethanol using *Clostridium ljungdahlii* ATCC No. 55988 and 55989.

A gaseous substrate in the form of syngas may provide CO to the fermentation. Syngas may include CO, $CO_2$ and $H_2$. However, relative amounts of CO, $CO_2$ and $H_2$ in the syngas may vary depending on how the syngas is generated. Some sources of syngas may include elevated levels of $CO_2$. Optimal conversions of CO into alcohols and other products and enhanced utilization of $CO_2$ may be dependent on relative levels of CO, $CO_2$ and $H_2$ in the syngas provided to the fermentation.

SUMMARY

A process is provided that is effective for reducing $CO_2$ emissions, enhancing STY and/or increasing cell density. The process allows for utilization of syngas from different sources by controlling concentration levels of CO, $CO_2$ and $H_2$ in syngas provided to the fermentation and by controlling relative concentrations of CO, $CO_2$ and $H_2$ in the syngas provided to the fermentation.

In one aspect, a process for treating off-gas from a CO fermentation includes providing syngas to a first fermentation zone and fermenting the syngas to generate a first fermentor off-gas having a CO concentration of about 4 mole % or more CO. At least a portion of the first fermentor off-gas is provided to one or more subsequent fermentation zones. In another aspect, the first fermentation off-gas is blended with an $H_2$ containing gas in an amount effective for providing a gas with an $H_2$ to CO molar ratio of about 0.2 or more prior to being supplied to one or more subsequent fermentation zones. In yet another aspect, the first fermentation off-gas is blended with a CO containing gas in an amount effective for providing a gas with an $H_2$ to CO molar ratio of about 0.2 or more prior to being supplied to one or more subsequent fermentation zones.

In one aspect, a process for treating off-gas from a CO fermentation includes providing syngas to a first fermentation zone and fermenting the syngas. If the first fermentation zone off-gas includes about 4 mole % or more CO, then the first fermentation zone off-gas is provided to one or more subsequent fermentation zones. In another aspect, the first fermentation off-gas is blended with a CO containing gas in an amount effective for providing a gas having about 4 mole % or more CO prior to being supplied to one or more subsequent fermentation zones. In another aspect, the first fermentation off-gas is blended with an $H_2$ containing gas in an amount effective for providing a gas with an $H_2$ to CO molar ratio of about 0.2 or more prior to being supplied to one or more subsequent fermentation zones. In yet another aspect, the first fermentation zone off-gas is blended with a CO containing gas in an amount effective for providing a gas with an $H_2$ to CO molar ratio of about 0.2 or more prior to being supplied to one or more subsequent fermentation zones.

In one aspect, a process for treating off-gas from a CO fermentation includes providing syngas to a first fermentor and fermenting the syngas. If the first fermentor off-gas includes about 4 mole % or more CO, then the first fermentor off-gas is provided to one or more subsequent fermentors. In another aspect, the first fermentor off-gas is blended with a CO containing gas in an amount effective for providing a gas having about 4 mole % or more CO prior to being supplied to one or more subsequent fermentors. In another aspect, the first fermentor off-gas is blended with an $H_2$ containing gas in an amount effective for providing a gas with an $H_2$ to CO molar ratio of about 0.2 or more prior to being supplied to one or more subsequent fermentors. In yet another aspect, the first fermentor off-gas is blended with a CO containing gas in an amount effective for providing a gas with an $H_2$ to CO molar ratio of about 0.2 or more prior to being supplied to one or more subsequent fermentors.

In another aspect, a process is provided for producing alcohol from a syngas fermentation. The process includes providing syngas to a fermentor. The syngas provided to the fermentor has an $H_2$ to CO molar ratio of about 3.5 or more and a CO content of about 4 mole % or more. The syngas fermentation process is effective for providing an STY of about 1 g or more total alcohol/(L·day). In one aspect, the process may include blending $H_2$ with a high CO gas to provide a syngas with an $H_2$ to CO molar ratio of about 3.5 or more. The process is effective for reducing $CO_2$ emissions about 10% or more per gram of cell in the fermentor as compared to a process where the $H_2$ to CO molar ratio of the syngas is about 1.0 or less.

BRIEF DESCRIPTION OF FIGURES

The above and other aspects, features and advantages of several aspects of the process will be more apparent from the following figures.

Corresponding reference characters indicate corresponding components throughout the figures. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various aspects of the present process and apparatus. Also, common but well-understood elements that are useful or necessary in commercially feasible aspects are often not depicted in order to facilitate a less obstructed view of these various aspects.

DETAILED DESCRIPTION

Figure 1:
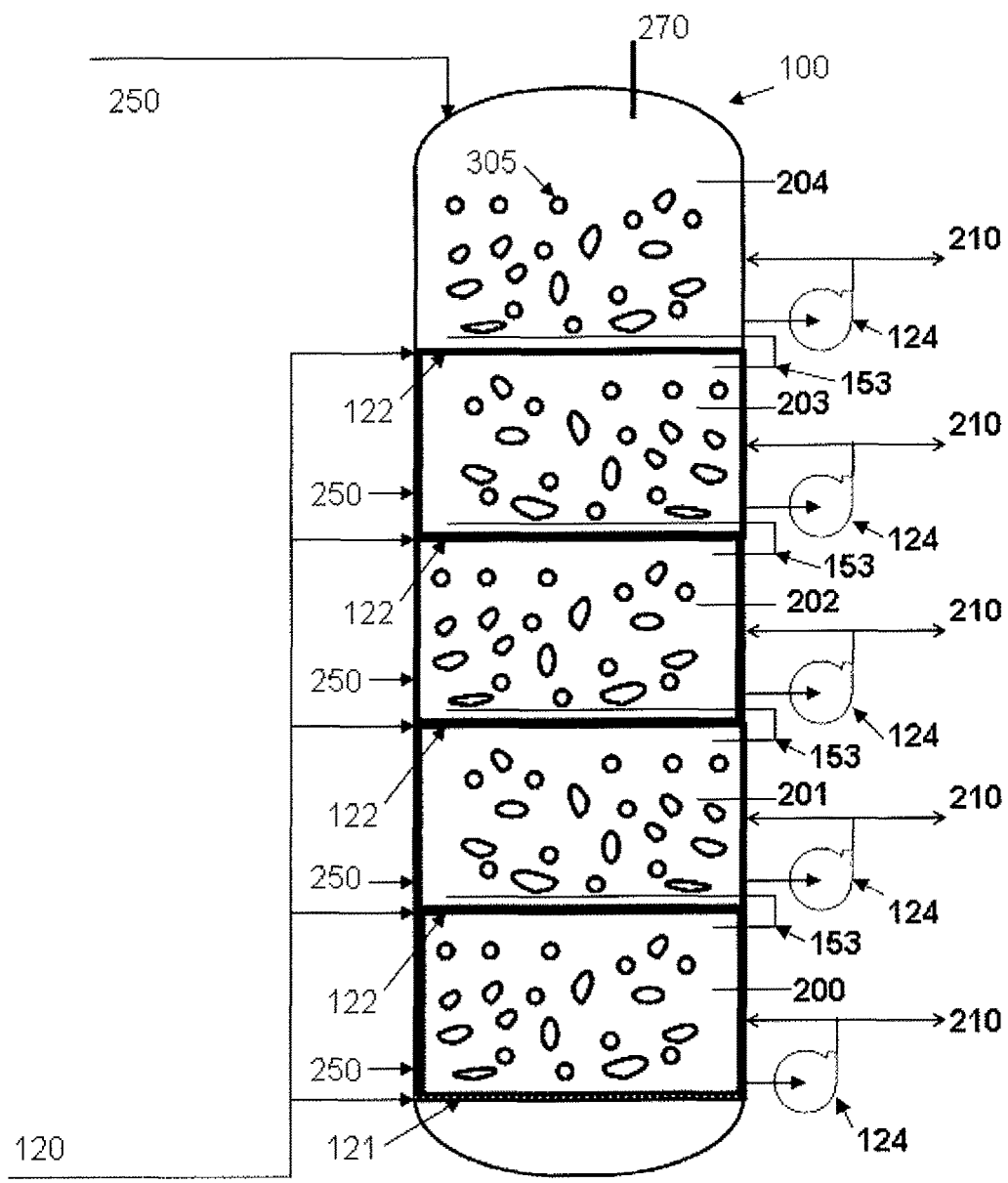
FIG. 1 is a perspective view of a fermentor with different fermentation zones.

The following description is not to be taken in a limiting sense, but is made merely for the purpose of describing the general principles of exemplary embodiments. The scope of the invention should be determined with reference to the claims.

DEFINITIONS

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is combustible and is often used as a fuel source or as an intermediate for the production of other chemicals.

The term "fermentor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

The terms "fermentation", "fermentation process" or "fermentation reaction" and the like are intended to encompass both the growth phase and product biosynthesis phase of the process. In one aspect, fermentation refers to conversion of CO to alcohol.

The term "cell density" means mass of microorganism cells per unit volume of fermentation broth, for example, grams/liter.

The term "off-gas" refers to all gas that exits the fermentor.

Syngas

Syngas may be provided from any know source. In one aspect, syngas may be sourced from gasification of carbonaceous materials. Gasification involves partial combustion of biomass in a restricted supply of oxygen. The resultant gas mainly includes CO and $H_2$. In this aspect, syngas will contain about 4 mole % or more CO, in another aspect, about 5 mole % or more CO, in another aspect, about 10 mole % or more CO, in another aspect, about 20 mole % or more CO, in another aspect, about 10 to about 100 mole % CO, in another aspect, about 20 to about 100 mole % CO, in another aspect, about 30 to about 90 mole % CO, in another aspect, about 40 to about 80 mole % CO, and in another aspect, about 50 to about 70 mole % CO. Some examples of suitable gasification methods and apparatus are provided in U.S. Ser. Nos. 61/516,667, 61/516,704 and 61/516,646, all of which were filed on Apr. 6, 2011, and in U.S. Ser. Nos. 13/427,144, 13/427,193 and 13/427,247, all of which were filed on Mar. 22, 2012, and all of which are incorporated herein by reference.

Depending on the syngas composition, the syngas may be provided directly to a fermentation process or may be further modified to include an appropriate $H_2$ to CO molar ratio. In one aspect, syngas provided to the fermentor has an $H_2$ to CO molar ratio of about 3.5 or more, in another aspect, about 4.0 or more, and in another aspect, about 5.0 or more. In another aspect, syngas provided to the fermentor may include about 40 mole percent or more CO plus $H_2$ and about 30 mole percent or less CO, in another aspect, about 50 mole percent or more CO plus $H_2$ and about 35 mole percent or less CO, and in another aspect, about 80 mole percent or more CO plus $H_2$ and about 20 mole percent or less CO.

In another aspect, the process has applicability to supporting the production of alcohol from gaseous substrates such as high volume CO-containing industrial flue gases. In some aspects, a gas that includes CO is derived from carbon containing waste, for example, industrial waste gases or from the gasification of other wastes. As such, the processes represent effective processes for capturing carbon that would otherwise be exhausted into the environment. Examples of industrial flue gases include gases produced during ferrous metal products manufacturing, non-ferrous products manufacturing, petroleum refining processes, gasification of coal, gasification of biomass, electric power production, carbon black production, ammonia production, methanol production and coke manufacturing.

In one aspect, a gas separator is configured to substantially separate at least one portion of the gas stream, wherein the portion includes one or more components. For example, the gas separator may separate $CO_2$ from a gas stream comprising the following components: CO, $CO_2$, $H_2$, wherein the $CO_2$ may be passed to a $CO_2$ remover and the remainder of the gas stream (comprising CO and $H_2$) may be passed to a bioreactor. Any gas separator known in the art may be utilized. In this aspect, syngas provided to the fermentor will have about 10 mole % or less $CO_2$, in another aspect, about 1 mole % or less $CO_2$, and in another aspect, about 0.1 mole % or less $CO_2$.

Certain gas streams may include a high concentration of CO and low concentrations of $H_2$. In one aspect, it may be desirable to optimize the composition of the substrate stream in order to achieve higher efficiency of alcohol production and/or overall carbon capture. For example, the concentration of $H_2$ in the substrate stream may be increased before the stream is passed to the bioreactor.

According to particular aspects of the invention, streams from two or more sources can be combined and/or blended to produce a desirable and/or optimized substrate stream. For example, a stream comprising a high concentration of CO, such as the exhaust from a steel mill converter, can be combined with a stream comprising high concentrations of $H_2$, such as the off-gas from a steel mill coke oven.

Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

Fermentor Design and Operation

In one aspect, a fermentor design may include different fermentation zones in the same fermentor. For example, a large fermentor or a bubble column type reactor may include different fermentation zones. Descriptions of fermentor designs are described in U.S. Ser. Nos. 13/471,827 and 13/471,858, both filed May 15, 2012, and U.S. Ser. No. 13/473,167, filed May 16, 2012, all of which are incorporated herein by reference.

As shown in FIG. 1, a fermentor 100 includes multiple fermentation zones 200. As shown, the fermentor 100 includes a first fermentation zone 200 and four additional fermentations zones 201, 202, 203, 204. In another aspect, the fermentor 100 may include two or more fermentation zones, and may includes from two to ten fermentation zones. A fermentation zone is defined as space above a gas inlet/sparger 121 and below a fermentation zone barrier 122, space above a zone sparger 153 and below a fermentation zone barrier 122, and/or space above a zone sparger 153 and the top of the fermentor 100. The fermentor 100 may also include pumps 124. The pumps 124 may be used for sample/product 210 removal.

In one aspect, fermentation zones are separated by fermentation zone barriers 122. Gases 305 may flow through each fermentation zone. Off-gas from any fermentation zone may be conveyed to a subsequent fermentation zone through a zone sparger 153. Off-gas from any fermentation zone may be analyzed.

In one aspect, syngas enters the fermentor 100 through a syngas supply 120. The syngas supply 120 provides syngas to the gas inlet/spargers 121. Medium and nutrients may be supplied to each fermentation zone 122 through medium/nutrient supply 250. Off-gas may exit each fermentation zone 122 through a zone sparger 153. Off-gas may exit the final fermentation zone through an off-gas port 270. Off-gas may be provided to a vent-gas boiler. The vent-gas boiler may be utilized to provide steam for energy production.

In accordance with one aspect, the fermentation process is started by addition of medium to the reactor vessel. Some examples of medium compositions are described in U.S. Ser. Nos. 61/650,098 and 61/650,093, filed May 22, 2012, and in U.S. Pat. No. 7,285,402, filed Jul. 23, 2001, all of which are incorporated herein by reference. The medium may be sterilized to remove undesirable microorganisms and the reactor is inoculated with the desired microorganisms. Sterilization may not always be required.

In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui*, *Acetoanaerobium noterae*, *Acetobacterium woodii*, *Alkalibaculum bacchi* CP11 (ATCC BAA-1772), *Blautia producta*, *Butyribacterium methylotrophicum*, *Caldanaerobacter subterraneous*, *Caldanaerobacter subterraneous pacificus*, *Carboxydothermus hydrogenoformans*, *Clostridium aceticum*, *Clostridium acetobutylicum*, *Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei*, *Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* O-52 (ATCC 55889), *Clostridium magnum*, *Clostridium pasteurianum* (DSM 525 of DSMZ Germany), *Clostridium ragsdali* P11 (ATCC BAA-622), *Clostridium scatologenes*, *Clostridium thermoaceticum*, *Clostridium ultunense*, *Desulfotomaculum kuznetsovii*, *Eubacterium limosum*, *Geobacter sulfurreducens*, *Methanosarcina acetivorans*, *Methanosarcina barkeri*, *Morrella thermoacetica*, *Morrella thermoautotrophica*, *Oxobacter pfennigii*, *Peptostreptococcus productus*, *Ruminococcus productus*, *Thermoanaerobacter kivui*, and mixtures thereof.

Upon inoculation, an initial feed gas supply rate is established effective for supplying the initial population of microorganisms. Off-gas is analyzed to determine the content of the effluent gas. Results of gas analysis are used to control feed gas rates. Upon reaching desired levels, liquid phase and cellular material is withdrawn from the reactor and replenished with medium. The process is effective for increasing cell density to about 2.0 grams/liter or more, in another aspect, about 2 to about 25 grams/liter, in another aspect, about 2 to about 20 grams/liter, in another aspect, about 2 to about 10 grams/liter, in another aspect, about 2 to about 8 grams/liter, in another aspect, about 3 to about 6 grams/liter, and in another aspect, about 4 to about 5 grams/liter.

In one aspect, syngas is supplied to a first fermentation zone 200. If a CO concentration in off-gas from the first fermentation zone 200 is about 4 mole % or greater, then at least a portion of the syngas being supplied to one or more subsequent fermentation zones through zone sparger 153.

Off-gas may be supplied to each fermentation zone one at a time or may be supplied to one or more fermentation zones simultaneously. In this aspect, syngas entering a fermentation zone will have about 20 mole % or more CO, in another aspect, about 30 mole % or more, in another aspect, about 40 mole % or more, and in another aspect, about 50 mole % or more.

In another aspect, syngas supplied to any fermentation zone will have an $H_2$ to CO molar ratio of about 0.2 or more, and from about 4 mole % to about 99.9 mole % CO. In another aspect, syngas entering any subsequent fermentation zone will have an $H_2$ to CO molar ratio of about 0.5 or more, in another aspect, about 1.0 or more, and in another aspect, about 3.5 or more.

Figure 2:
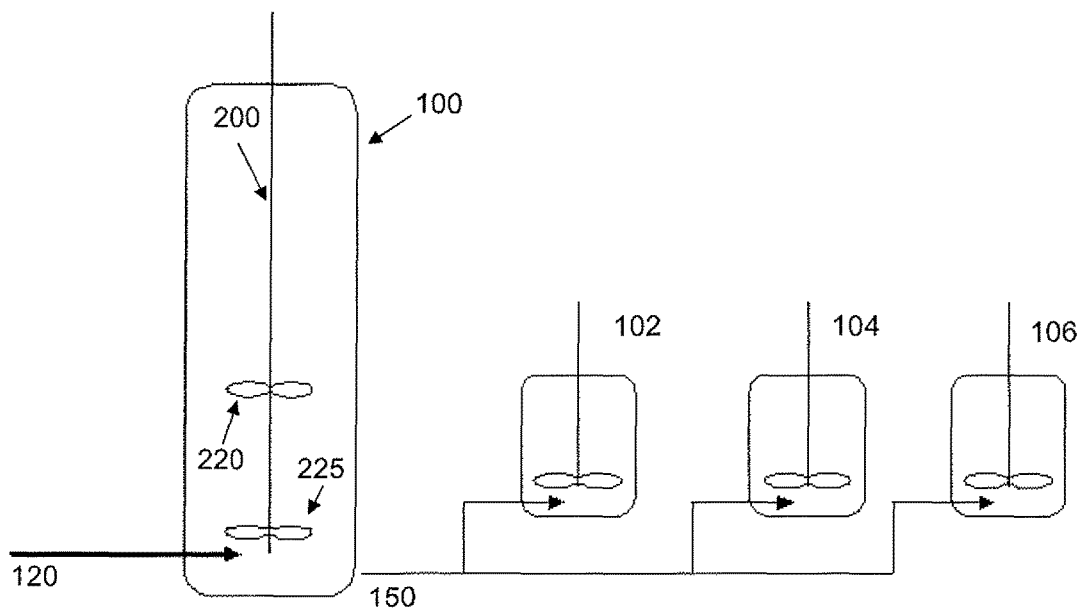
FIG. 2 is a perspective view of a series of fermentors where all fermentors subsequent to a first fermentor can each directly receive off-gas from the first fermentor.
Figure 3:
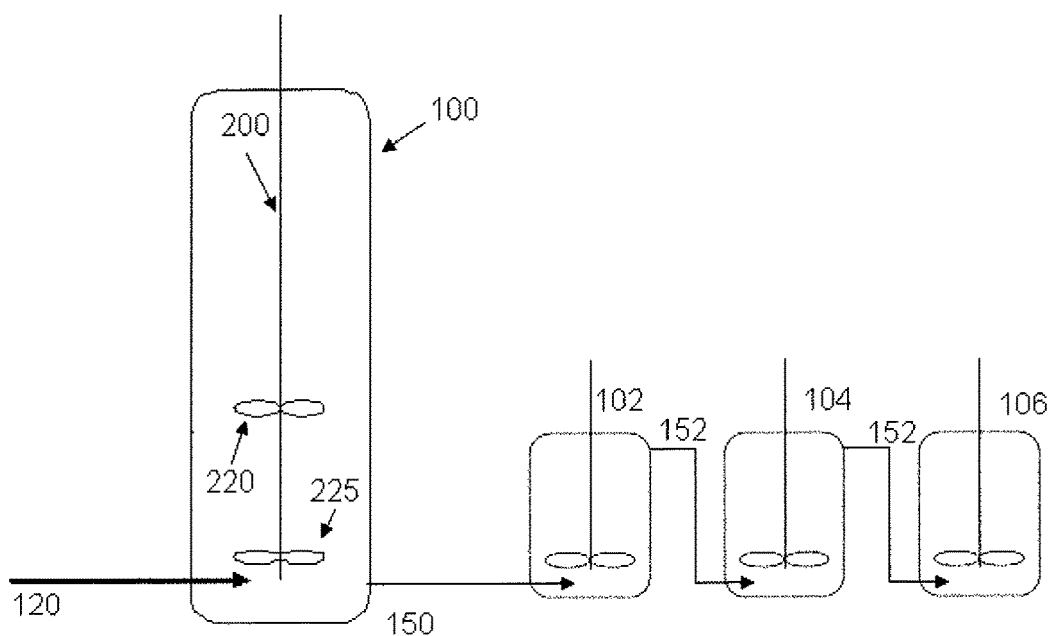
FIG. 3 is a perspective view of a series of fermentors where off-gas from each fermentor is transferred to a subsequent fermentor.

Another aspect of a fermentor design is shown in FIG. 2. In this aspect, the design includes a first fermentor 100 connected in series to subsequent fermentors, such as for example, second fermentor 102, third fermentor 104, and fourth fermentor 106. The design may include any number of subsequent fermentors from 1 to about 10 (for example, 1, 2, 3, 4, 5, 6, 7, 8, 9 or 10 subsequent fermentors).

In one aspect, syngas enters the first fermentor 100 through a gas inlet/sparger 120. Dispersion of the syngas and further mixing is accomplished with at least one gas dispersion impeller 225 and at least one mixing impeller 220 which are coupled to a drive shaft 200.

Fermentor off-gas 150 may be conveyed to the one or more subsequent bioreactors. Fermentor off-gas may be supplied to each subsequent fermentor one at a time in series, or may be supplied to one or more subsequent fermentors simultaneously in parallel. In this aspect, fermentor off-gas supplied to any subsequent fermentor will have an $H_2$ to CO molar ratio of about 0.2 or more and about 4 mole % or more CO. In another aspect, the fermentor off-gas entering any subsequent fermentor will have an $H_2$ to CO molar ratio of about 0.25 or more, in another aspect, about 0.5 or more, in another aspect, about 1.0 or more, in another aspect, about 1.5 or more, and in another aspect, about 3.5 or more. In one aspect, the fermentor off-gas entering any subsequent fermentor will have about 20 mole % or more CO, in another aspect, about 30 mole % or more, in another aspect, about 40 mole % or more, and in another aspect, about 50 mole % or more.

Another aspect of a fermentor design is shown in FIG. 2. In this aspect, the design includes a first fermentor 100 connected in series to subsequent fermentors, such as for example, second fermentor 102, third fermentor 104, and fourth fermentor 106. The design may include any number of subsequent fermentors from 1 to about 10 (for example, 1, 2, 3, 4, 5, 6, 7, 8, 9 or 10 subsequent fermentors). Fermentor off-gas 150 may be conveyed from a first fermentor 100 to a subsequent fermentor 102. Fermentor off-gas from any subsequent fermentor 152 may then be conveyed to any subsequent fermentor.

In the fermentor design shown in FIG. 2, fermentor off-gas 150 may be conveyed to the one or more subsequent bioreactors. Fermentor off-gas may be supplied to each subsequent fermentor. In this aspect, fermentor off-gas supplied to any subsequent fermentor will have an $H_2$ to CO molar ratio of about 0.2 or more, about 4 mole % or more CO. In another aspect, the fermentor off-gas entering any subsequent fermentor will have an $H_2$ to CO molar ratio of about 0.25 or more, in another aspect, about 0.5 or more, in another aspect, about 1.0 or more, in another aspect, about 1.5 or more, and in another aspect, about 3.5 or more. In one aspect, the fermentor off-gas entering any subsequent fermentor will have about 20 mole % or more CO, in another aspect, about 30 mole % or more, in another aspect, about 40 mole % or more, and in another aspect, about 50 mole % or more.

In another aspect, off-gas from a first or any subsequent fermentor may be provided to a vent-gas boiler. The vent-gas boiler may be utilized to provide steam for energy production.

Alcohol Productivity

Certain ratios of $H_2$ to CO and/or $CO_2$ to CO are effective for providing enhanced STY. In this aspect, the process is effective for providing a STY (space time yield) of about 1 gram or more total alcohol/(L·day). In another aspect, the process is effective for providing a providing a STY of at least about 10 g total alcohol/(L·day). Possible STY values include about 10 g total alcohol/(L·day) to about 200 g total alcohol/(L·day), in another aspect, about 10 g total alcohol/(L·day) to about 160 g total alcohol/(L·day), in another aspect, about 10 g total alcohol/(L·day) to about 120 g total alcohol/(L·day), in another aspect, about 10 g total alcohol/(L·day) to about 80 g total alcohol/(L·day), in another aspect, about 20 g total alcohol/(L·day) to about 140 g total alcohol/(L·day), in another aspect, about 20 g total alcohol/(L·day) to about 100 g total alcohol/(L·day), in another aspect, about 40 g total alcohol/(L·day) to about 140 g total alcohol/(L·day), and in another aspect, about 40 g total alcohol/(L·day) to about 100 g total alcohol/(L·day).

As used herein, "total alcohol" includes ethanol, butanol, propanol and methanol. In one aspect, the total alcohol may include at least about 80 weight percent or more ethanol. In another aspect, total alcohol may include at least about 25 weight percent or less butanol.

In a related aspect, productivity may be expressed as STY (space time yield expressed as g ethanol/(L·day). In this aspect, the process is effective for providing a STY (space time yield) of at least about 10 g ethanol/(L·day). Possible STY values include about 10 g ethanol/(L·day) to about 200 g ethanol/(L·day), in another aspect, about 10 g ethanol/(L·day) to about 160 g ethanol/(L·day), in another aspect, about 10 g ethanol/(L·day) to about 120 g ethanol/(L·day), in another aspect, about 10 g ethanol/(L·day) to about 80 g ethanol/(L·day), in another aspect, about 20 g ethanol/(L·day) to about 140 g ethanol/(L·day), in another aspect, about 20 g ethanol/(L·day) to about 100 g ethanol/(L·day), in another aspect, about 40 g ethanol/(L·day) to about 140 g ethanol/(L·day), and in another aspect, about 40 g ethanol/(L·day) to about 100 g ethanol/(L·day).

Reduction in $CO_2$ Emissions

In one aspect, the process is effective for reducing $CO_2$ emissions about 10% or more, in another aspect, about 15% or more, and in another aspect, about 20% or more as compared to a process where the $H_2$ to CO molar ratio of the syngas is less than about 1.0. $H_2$ to CO molar ratios relate to reductions in $CO_2$ emissions as follows.

| $H_2$ to CO molar ratio | % reduction in $CO_2$ emissions |
| --- | --- |
| 0 | 0 |
| 0.5 | 4 |
| 1 | 7.4 |
| 1.8 | 21 |
| 3 | 30 |

In this aspect, $CO_2$ emissions are measured at an effluent gas of the reactor using gas chromatography. Any know methods may be used to determine $CO_2$ emissions.

While the invention herein disclosed has been described by means of specific embodiments, examples and applications thereof, numerous modifications and variations could be made thereto by those skilled in the art without departing from the scope of the invention set forth in the claims.

What is claimed is:

1. A process of treating off-gas from a CO fermentation, the process comprising:

providing syngas to a first fermentor;

fermenting the syngas with a bacteria selected from the group consisting of *Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), and mixtures thereof;

generating a first fermentor off-gas; and providing at least a portion of the first fermentor off-gas to one or more subsequent fermenters, wherein the first fermentor off-gas provided to the one or more subsequent fermenters has 4 mole % or more CO, and 10 mole % or less $CO_2$, wherein the first fermentor off-gas is blended with an $H_2$ containing gas in an amount to provide a ratio of $H_2$ to CO molar ratio of 1.0 or more prior to being supplied to one or more subsequent fermenters, wherein the process provides an STY of 1.0 gram or more total alcohol/(L·day) and reduces $CO_2$ emissions 10% or more.

2. The process of claim 1 wherein the first fermentor off-gas is provided to the subsequent fermentors operating in parallel.

3. The process of claim 1 wherein the first fermentor off-gas is provided to the subsequent fermentors operating in series.

4. The process of claim 1 wherein the first and subsequent fermentors are different fermentation zones in a fermentor.

5. The process of claim 1 wherein off-gas from a first fermentor or any subsequent fermentor is supplied to a vent-gas boiler.

6. The process of claim 1 wherein the first fermentor off-gas is blended with a CO-containing gas to provide a gas having 4 mole % or more CO prior to being supplied to the one or more subsequent fermentors.

7. The process of claim 1 wherein the first fermentor off-gas is blended with a CO containing gas in an amount effective for providing, a ratio of $H_2$ to CO molar ratio of 1.0 or more prior to being supplied to one or more subsequent fermentors.

8. The process of claim 1 wherein the first fermentor is effective for providing an STY of 1.0 gram or more total alcohol/(L·day).

* * * * *